(12) United States Patent
Luchetti et al.

(10) Patent No.: US 11,051,816 B2
(45) Date of Patent: Jul. 6, 2021

(54) INCISION AND CLOSURE SURGICAL DEVICE

(71) Applicants: Pablo Cristian Luchetti, Buenos Aires (AR); Luciano Poggi, Buenos Aires (AR)

(72) Inventors: Pablo Cristian Luchetti, Buenos Aires (AR); Luciano Poggi, Buenos Aires (AR)

(73) Assignee: INCLODE, Buenos Aires (AR)

( * ) Notice: Subject to any disclaimer, the term of this patent is extended or adjusted under 35 U.S.C. 154(b) by 189 days.

(21) Appl. No.: 16/448,073

(22) Filed: Jun. 21, 2019

(65) Prior Publication Data
US 2019/0357908 A1 Nov. 28, 2019

(30) Foreign Application Priority Data

Jun. 28, 2018 (AR) .............................. 20180101804

(51) Int. Cl.
*A61B 17/08* (2006.01)
*A61B 17/00* (2006.01)

(52) U.S. Cl.
CPC .. *A61B 17/085* (2013.01); *A61B 2017/00862* (2013.01); *A61B 2017/00876* (2013.01); *A61B 2017/00884* (2013.01); *A61B 2017/00951* (2013.01)

(58) Field of Classification Search
CPC ........ A61B 17/085; A61B 2017/00862; A61B 2017/00876; A61B 2017/00884; A61B 2017/00951; A61B 2017/081
See application file for complete search history.

(56) References Cited

U.S. PATENT DOCUMENTS

| 2013/0066365 A1* | 3/2013 | Belson ................... A61B 17/08 |
| | | 606/216 |
| 2013/0296930 A1* | 11/2013 | Belson ................. A61B 17/085 |
| | | 606/216 |

* cited by examiner

*Primary Examiner* — Melanie R Tyson

(57) ABSTRACT

Incision and closure surgical device containing a guide for cutting instruments and a sutureless wound closure mechanism. A stick-to-skin tape has a central slit whose edges are reinforced by two strips that delimit a central incision groove. A removable central partition maintains a constant separation between the elastomeric strips before making the incision. A series of transverse conduits pass through the elastomeric strips and serve for drainage of the wound and for coupling the closing mechanism of the device. At the conclusion of the surgery, a removable pressure or magnetic closure comprises two bilateral flexible strips that are hooked together to approximate the elastomeric strips while facing the edges of the underlying wound. A complementary removable adapter element for laparoscopic surgery serves as a support for a trocar and as a gas containment valve. Another complementary removable adapter element serves as an ogive-shaped cutting guide for cutaneous excisional surgery.

1 Claim, 9 Drawing Sheets

INCISION AND CLOSURE SURGICAL DEVICE

BACKGROUND OF THE INVENTION

1. Field of the Invention

The present invention fits within medical devices designed to assist in operative surgery and is particularly grouped within devices for incision and closure of the skin that transmit mechanical energy to the tissues.

2. Description of the Related Art

In connection with the prior art especially intended for the realization and repair of surgical incisions, the present invention is closely linked to devices or instruments that include a groove or channel to guide the displacement of a surgical cutting instrument and devices that include a sutureless wound closure mechanism. Some examples of these techniques can be seen in U.S. Pat. Nos. 8,777,986 B2, 7,594,914 B2, 4,905,694, 4,114,624, 3,983,878, 3,568,276, 3,516,409 and U.S. Pat. Appl. Pub. No. 2013/0066365. Within this category, the devices that most resemble the present invention include a stick-to-skin adhesive tape placed around the wound, which serves as the structural means on which a closure is operated to close the incision.

Although the abovementioned devices allow a more precise control of the incision and offer a less invasive closure than sutures and clamps, none of these examples contemplates certain biological factors related to damage and repair of a surgical wound. Firstly, any incision generates a loss of substance caused by necrosis and retraction of the skin surrounding the cut. The lost tissue will produce a slit of dead space that must be recovered at the time of joining the edges of the wound, either by means of a suture or through any closing mechanism that pulls the adjacent skin. For its part, conventional suture can achieve this goal, since the surgeon faces—and even evert—the edges of the wound as much as it is appropriate, by just applying more or less tension to the suture. On the contrary, techniques of abovementioned patents do not contemplate the uneven retraction between the edges of an inert tape and the edges of the underlying incised skin. Although said techniques allow joining and repositioning the edges of the tape in its location prior to the incision, they will not be able to fully face the retracted edges of the underlying skin. On the other hand, after the incision is made, the wound healing process is unleashed, including hemostasis, inflammation, proliferation and remodeling of tissues. These events modify the microenvironment of the skin, including changes in the rate of fluid secretion. None of the abovementioned patents contemplates the inclusion of an effective drainage system that allows the evacuation of both physiological and pathological fluids that could originate in the wound. This defect in the drainage of the wound increases the risk of maceration of the skin and the loss of effectiveness of the stick-to-skin adhesive, favoring the detachment of the tape. Said examples neither include closure systems that are compliant with possible increases in volume and tension in a surgical wound, which are very common in case of collections such as seromas, hematomas and abscesses. In such cases, it is necessary that both the tape and the closure system accompany the movement of the skin to reduce the risk of tape detaching. In other cases, some complications such as surgical site infection usually require partial or total early removal of the closure device. None of the abovementioned patents contemplates the possibility of partially uncoupling the closure system, a resource equivalent to "dropping stitches" in the sutured wounds. In many cases, the possibility of an early removal of the entire device is not contemplated, since the proposed adhesive is so aggressive (e.g. cyanoacrylate) that it would only allow an immediate removal of the tape at the expense of undesirable skin damage. Finally, U.S. Pat. Appl. Pub. No. 2013/0066365 is the only one of the aforementioned publications that has considered adapting the use of the device to address some complications related to the techniques of laparoscopic surgery and excisional surgery of the skin. In this sense, although laparoscopic surgery has innumerable advantages over open surgery, it still presents complications related to the excessive flow of the gas used to achieve the pneumoperitoneum required in this technique. Other inconveniences may result from the involuntary sliding of the trocar during surgery. Such movement could increase the risk of hematoma, surgical site infection, eventrations and postoperative pain. On the other hand, excisional skin surgery uses an elliptical incision whose geometry must be precise in order to avoid unsightly scarring.

Unlike the abovementioned prior art, the present invention contemplates the dynamic circumstances of the healing process of a wound. On the one hand, the device has a central slit in the adhesive tape that leaves exposed to the air a longitudinal skin surface, on which the incision will be made. Said slit, and the whole incisional groove that surrounds it, both have a width greater than the blade of any conventional cutting instrument, allowing that even after the loss of tissue, the edges of the incised skin remain contained within said groove. At the moment of closing the incision, the closure mechanism compresses the elastomeric strips causing the lateral walls of the incisional groove to touch each other, succeeding to close said groove completely and guaranteeing the apposition of the edges of the underlying wound. On the other hand, the present invention presents a series of drainage ducts communicating the central slit of the adhesive tape with the outside. Said mechanism of fluid discharge significantly reduces the risk of accumulation of secretions, and the consequent risk of detachment of the tape among other complications. Likewise, the present device contemplates the need to accompany an eventual swelling of the skin and soft parts by incorporating elastomeric materials in all its components: adhesive, tape backing, closing strips and the coupled closure system. In addition to the choice of said materials, the closing mechanism itself has anchoring points spaced apart from one another, allowing the elongation of the strip segments interposed between two of said anchor points. This separate-anchorage-points system also allows the possibility of partially uncoupling the closure system only at the points of union where required. Besides, the type of pressure sensitive adhesive used in the present device allows a complete removal of the skin tape at any time during the surgical procedure or during the postoperative period, without this event generating additional damage to the skin. On the other hand, the present device includes an adapter for anchoring a conventional laparoscopic surgery trocar. Said accessory fulfills the purpose of preventing spontaneous trocar slippage and the purpose of effectively sealing its entry orifice to reduce the leakage of the gas used to achieve the pneumoperitoneum. Finally, the present invention includes another adapter element for excisional skin surgery, which is formed by an ogive-shaped ring that is placed in the incisional groove and serves as a precise cutting guide for the ablation of skin lesions.

Unlike existing techniques, the present invention was designed to be placed on the skin prior to making the incision, not only with the aim of obtaining a copy of the intact skin, but also to adapt to changes in volume and moisture that occur during healing, and then succeed in reconstituting said copy at the time of closure, through its properties of porosity, elongation and elastic memory.

BRIEF SUMMARY OF THE INVENTION

The present incision and closure surgical device comprises a guide for cutting instruments and a sutureless wound closure mechanism. A stick-to-skin adhesive tape has a central slit which edges are reinforced by two elastomeric strips that delimit an incision groove. The main objects of the device include: a removable central partition or septum to keep the elastomeric strips separated before the incision, a series of lateral conduits that pass through the elastomeric strips that serve for the drainage and the anchoring of the closing mechanism, a removable closure formed by two flexible strips provided with magnetic or snap-fit teeth, a removable adapter for securing and sealing a trocar for laparoscopic surgery, and a removable ogive-shaped ring that fits into the incision groove and serves as a guide for cutting instruments in excisional skin surgery.

DETAILED DESCRIPTION OF THE INVENTION

Figure 1:
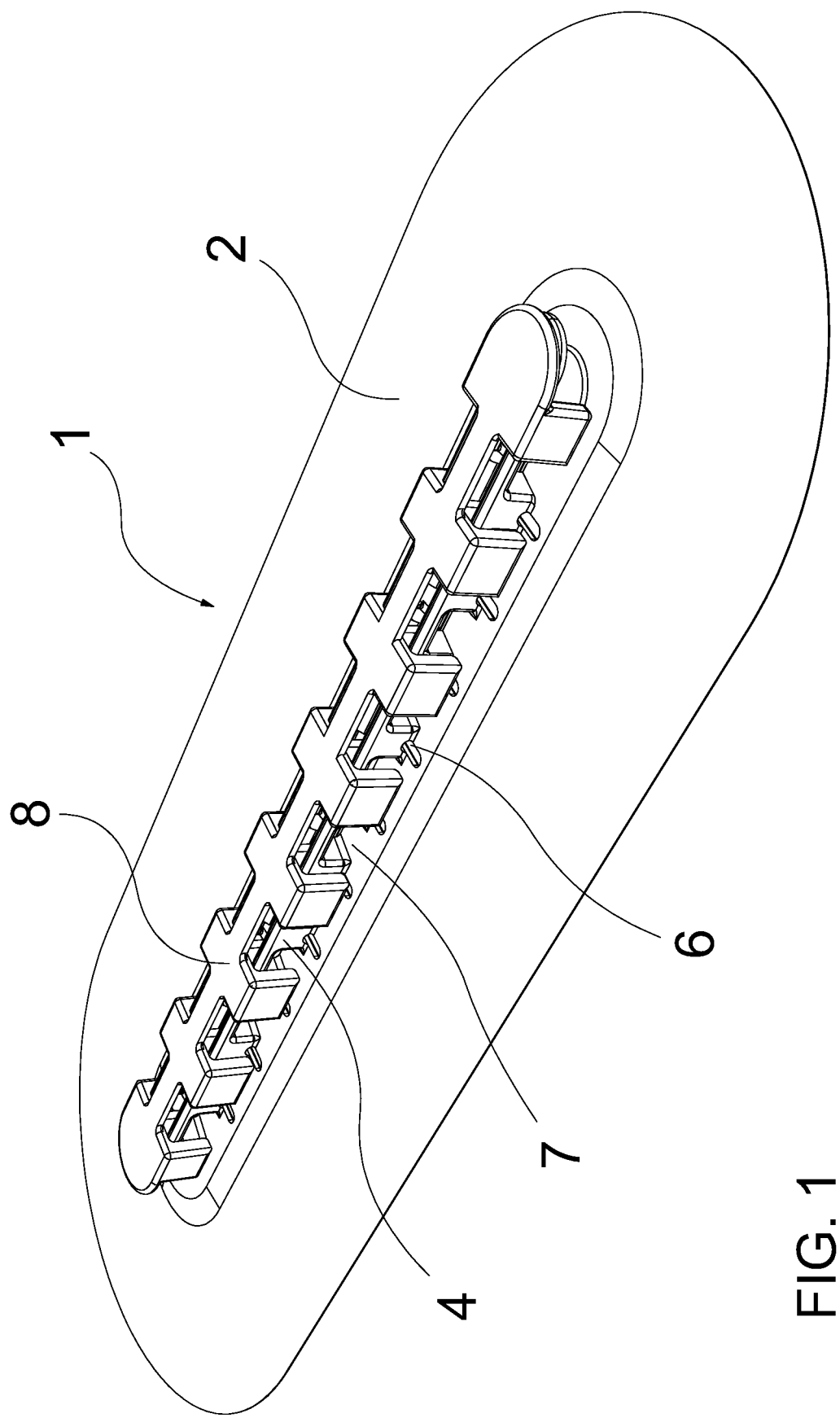
FIG. 1 shows a perspective view of the upper face of the skin incision and closure surgical device before being placed in a surgical site.
Figure 2:
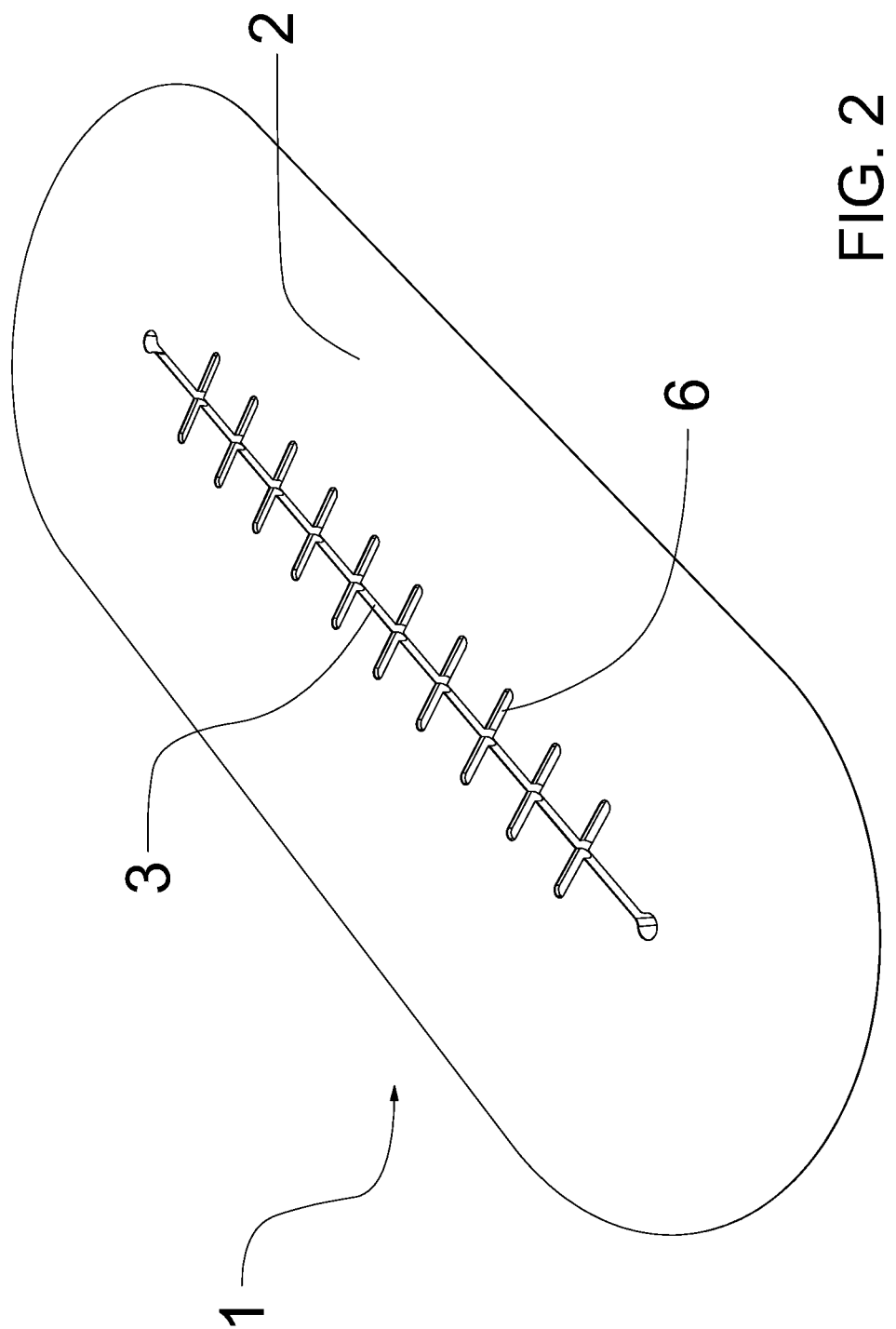
FIG. 2 shows a perspective view of the lower face of the device before being placed on a surgical site.
Figure 3:
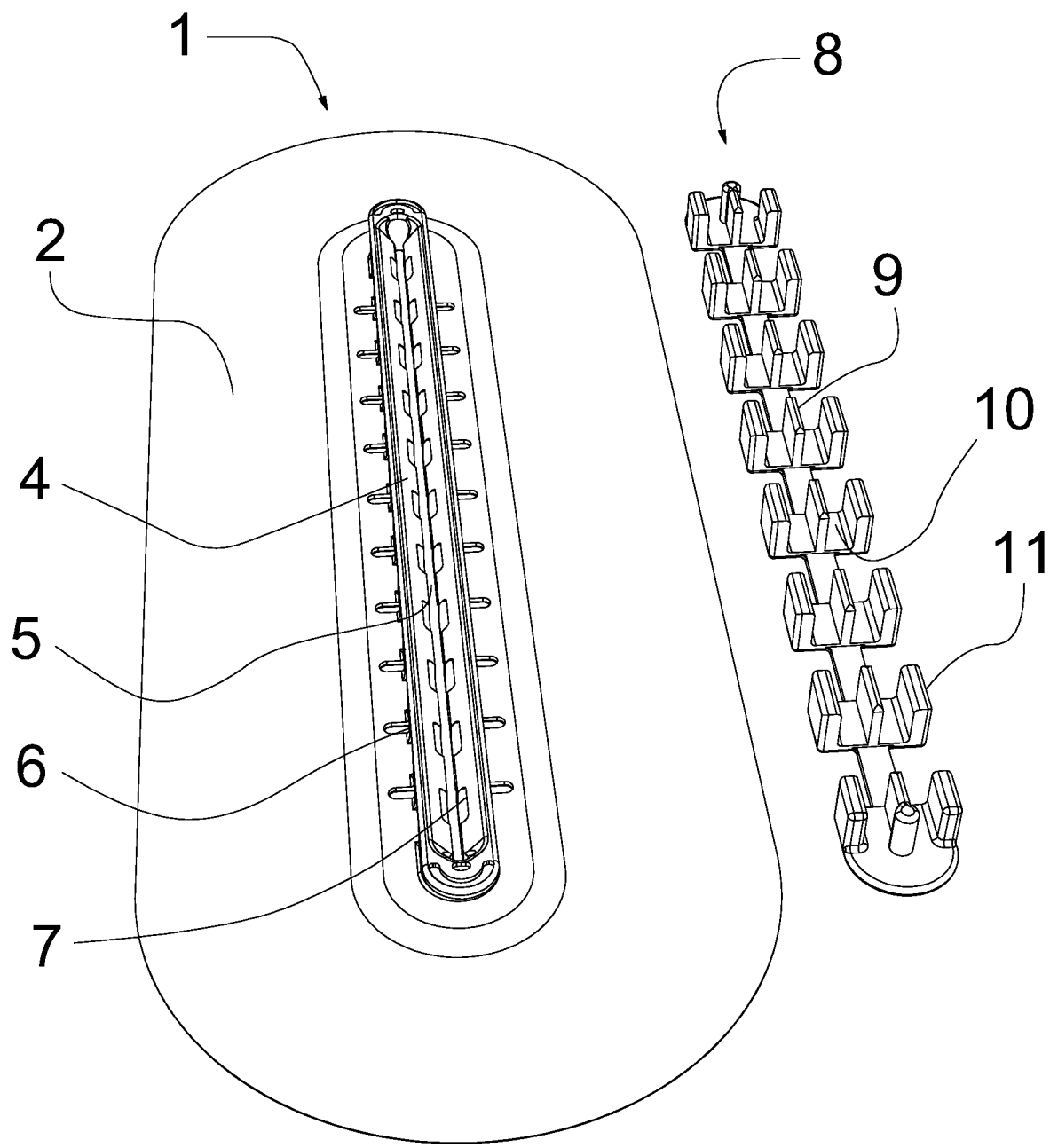
FIG. 3 shows a perspective view of the device already adhered to the operative site of the skin, with the central partition removed to make the incision.
Figure 4:
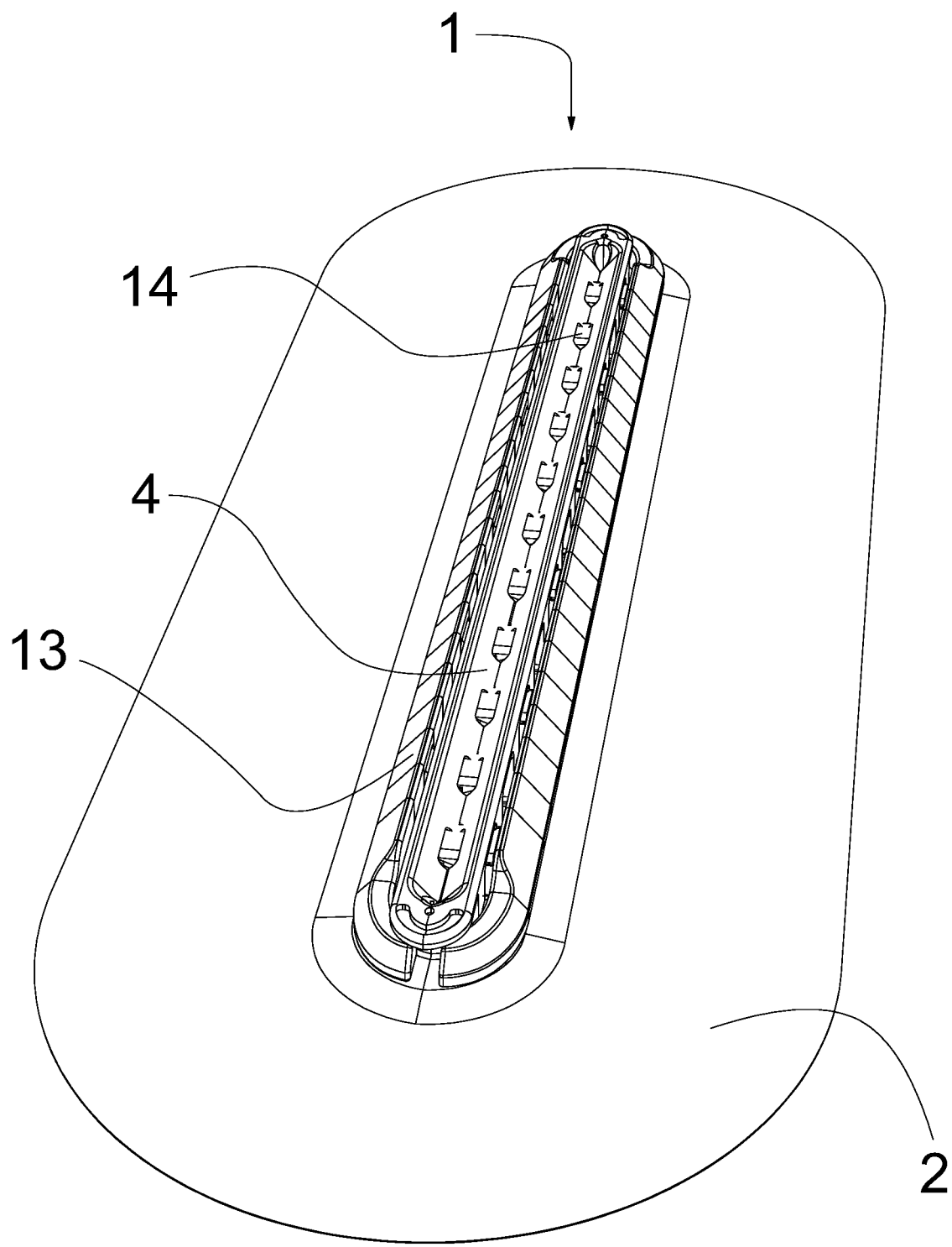
FIG. 4 shows a perspective view of the device with the pressure closure mechanism already engaged, after the surgical procedure is finished.
Figure 5:
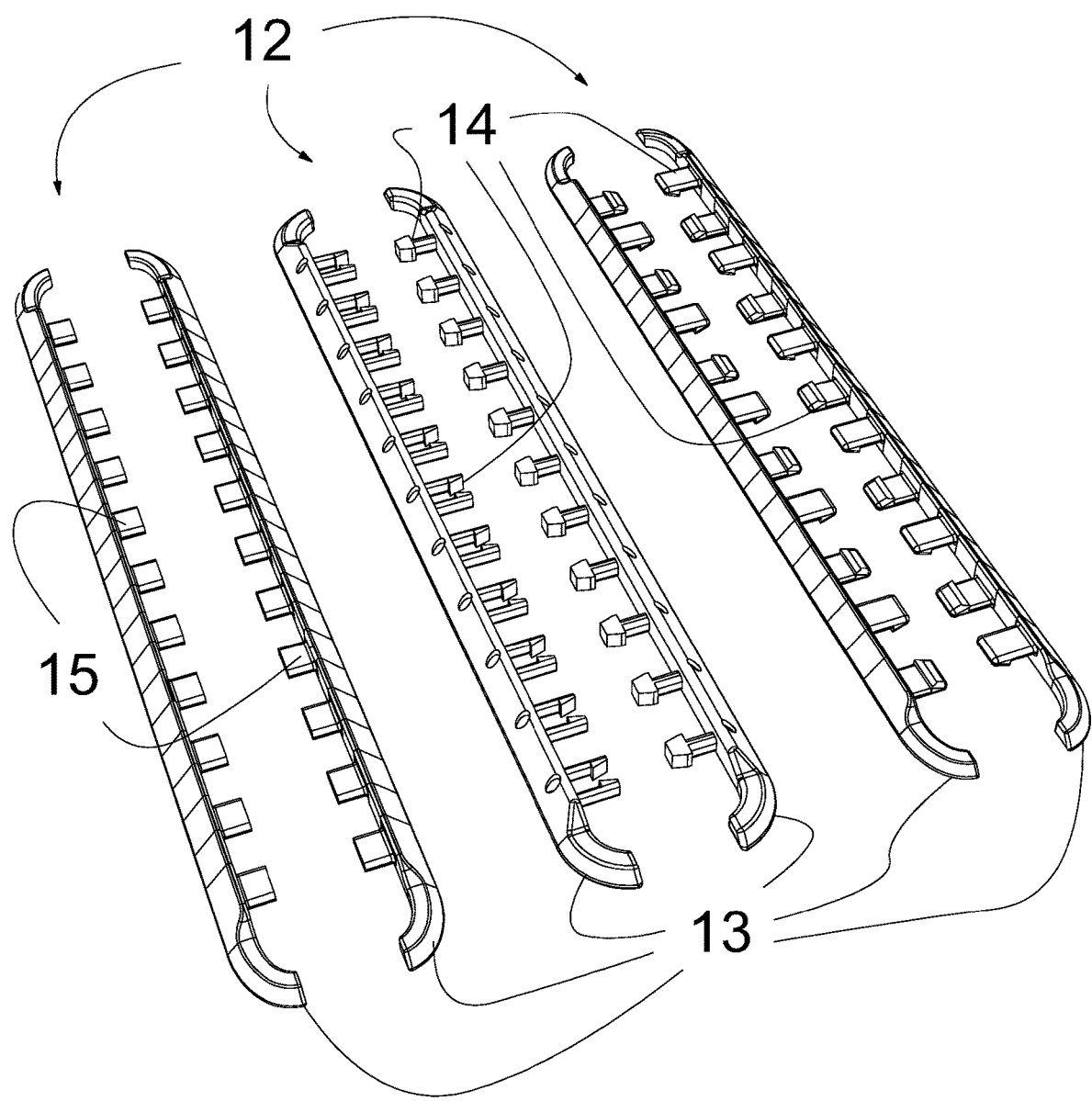
FIG. 5 shows a perspective view of the pressure closure and the magnetic closure mechanisms of the device before being coupled for wound closure.
Figure 6:
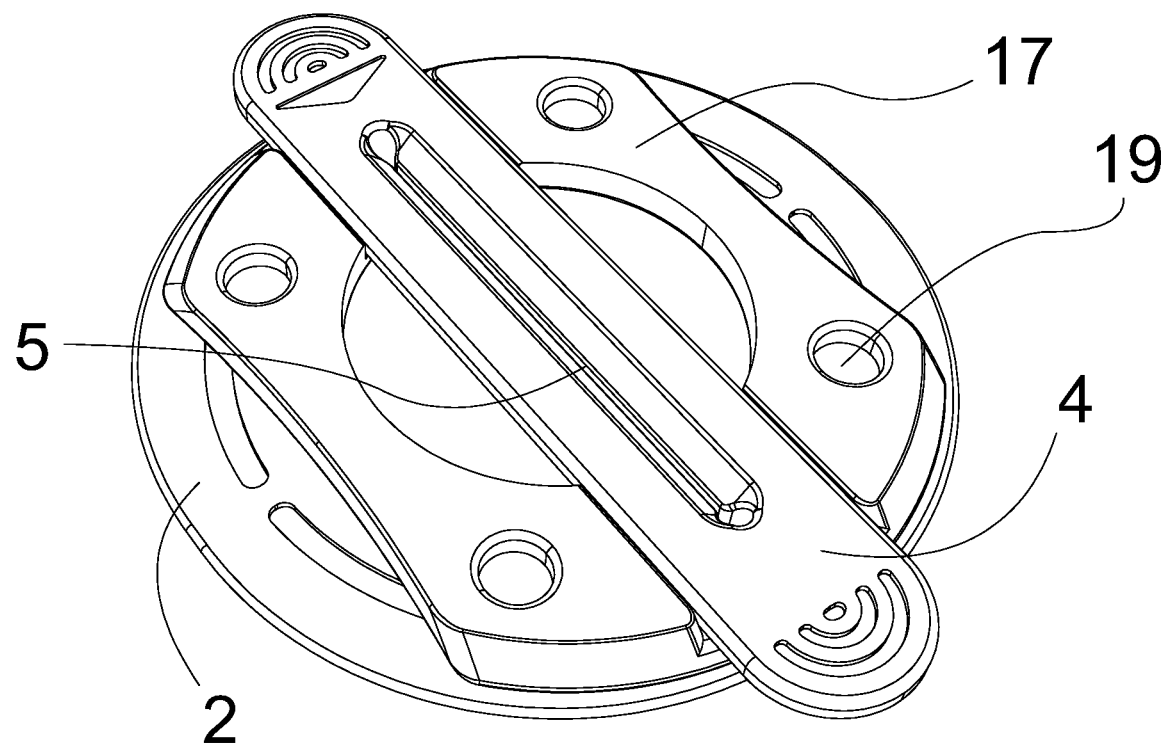
FIG. 6 shows a perspective view of the device in its version adapted for laparoscopic surgery, with the fixing washer placed and the central septum already removed to make the incision.
Figure 7:
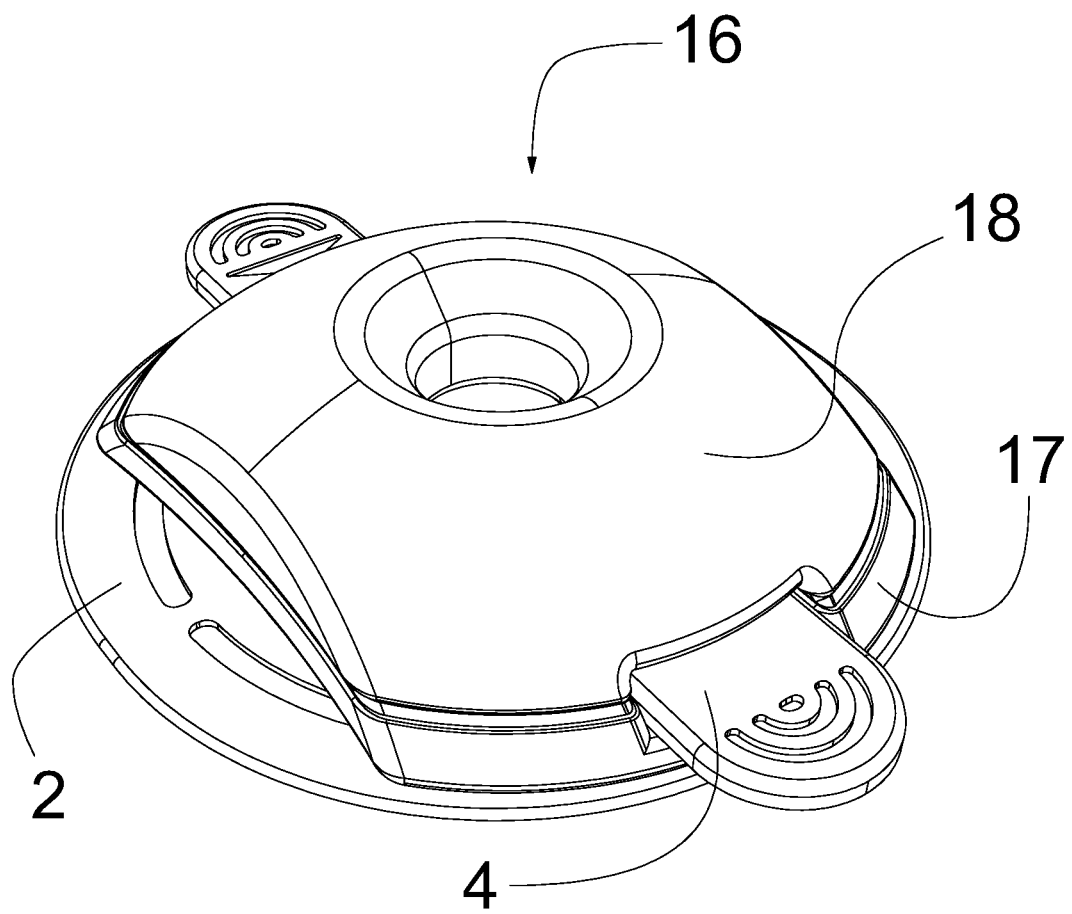
FIG. 7 shows a perspective view of the device in its version for laparoscopic surgery, with the cupola of the adapter already coupled and ready to receive a conventional trocar.
Figure 8:
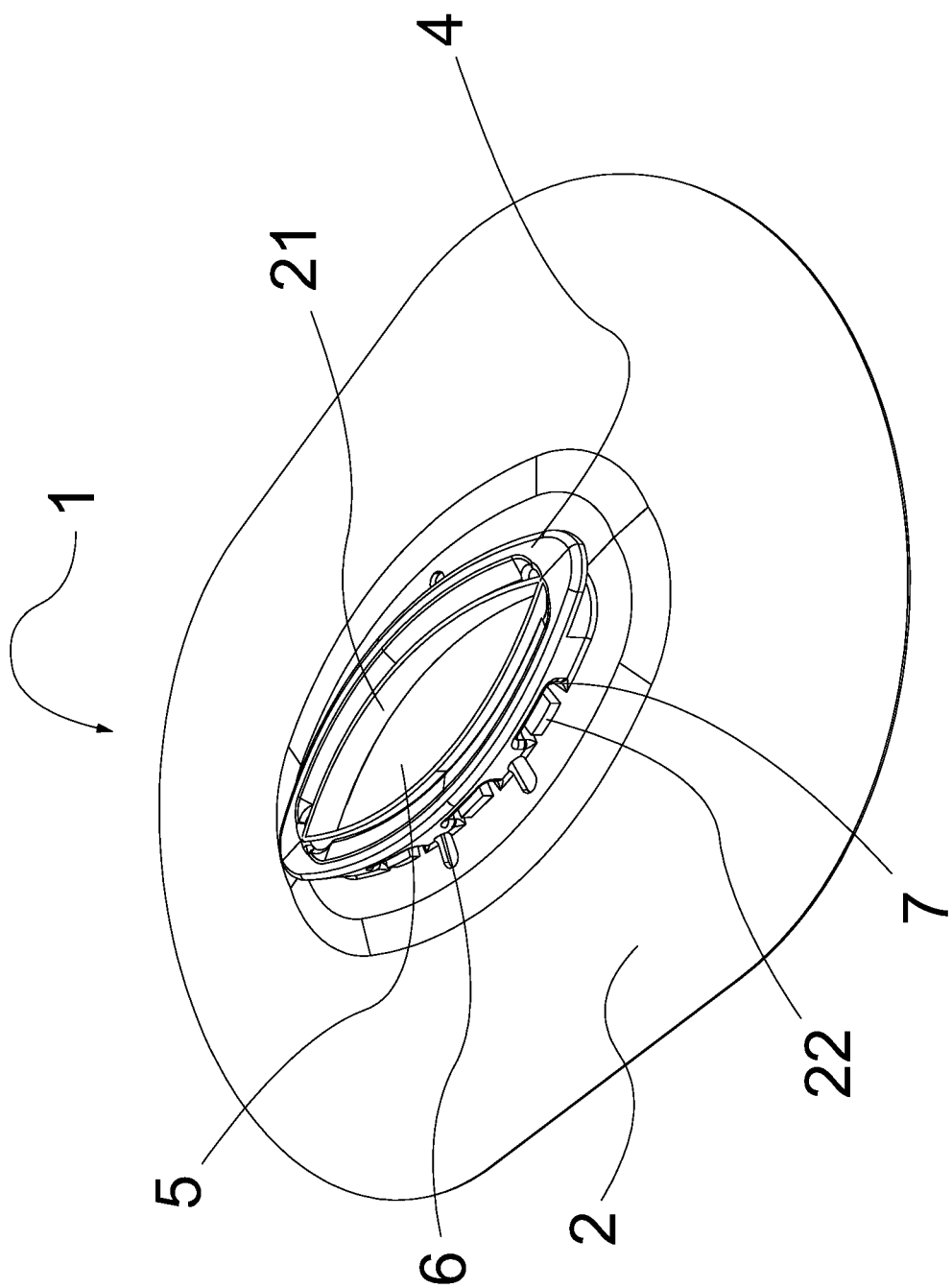
FIG. 8 shows a perspective view of the device in its version for excisional surgery of skin, with the ogive-shaped ring already coupled to be able to make the elliptical incision.
Figure 9:
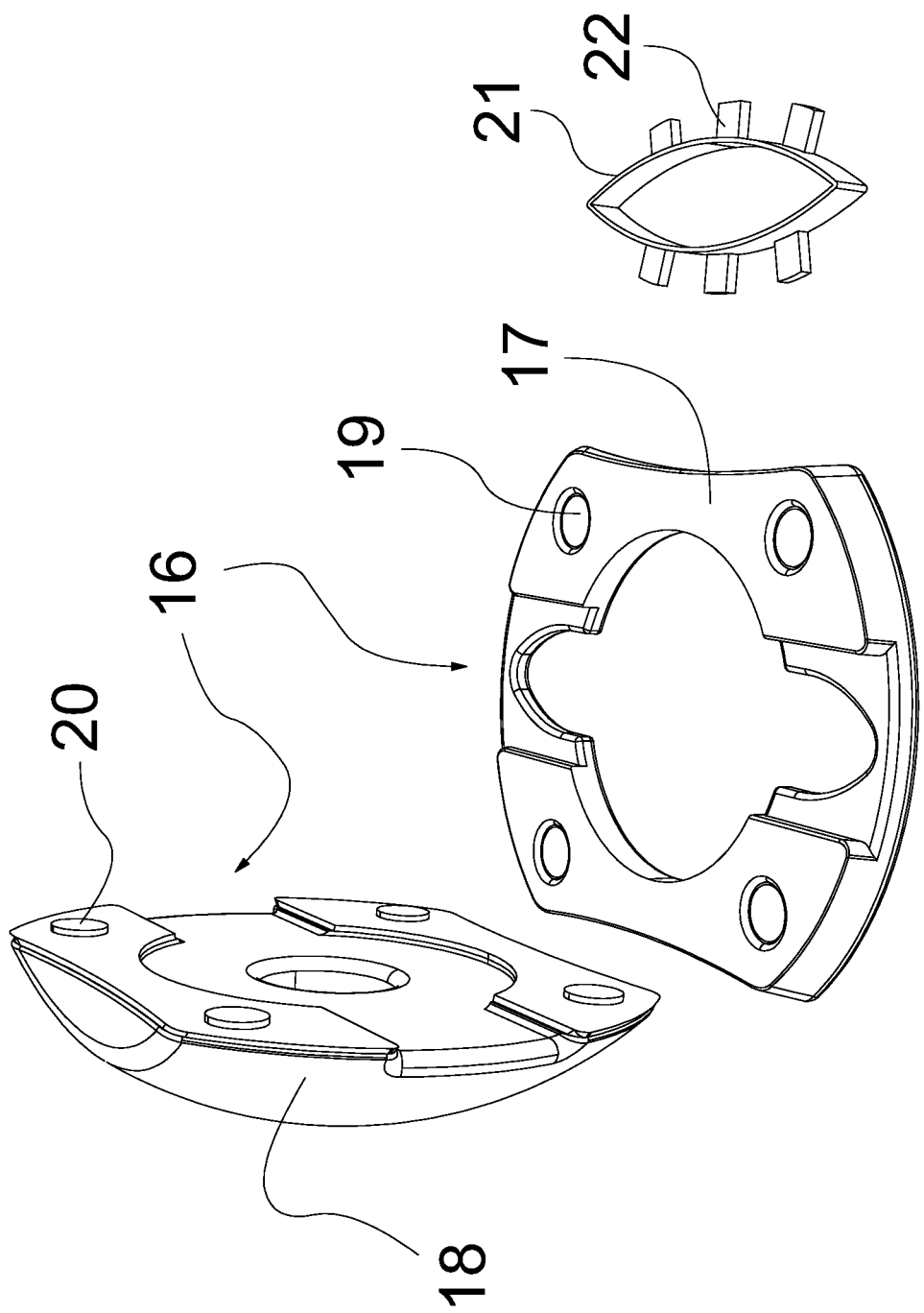
FIG. 9 shows a perspective view of the adapter for laparoscopic surgery and the ogive-shaped ring for excisional skin surgery, after being removed from the device.

In all the figures described above, the same reference numbers indicate identical or corresponding elements.

The present skin incision and closure surgical device (1) consists of a stick-to-skin adhesive tape (2) having a central slit (3) which edges are reinforced by two longitudinal elastomeric strips (4) that define a central incision groove (5). The elastomeric strips (4) are traversed by a series of lateral conduits connecting the incision groove (5) with the outer wall of the strips (4). Some of these ducts are smaller in diameter (6) than the others (7) and serve as drainage pathways for the surgical wound. The larger diameter ducts (7) serve as an anchoring site for the closure mechanism (12) of the medical device (1).

A removable longitudinal partition (8) has segments of T-shaped section, with vertical sheets (9) occupying the incision groove (5), and with horizontal sheets (10) that rest on the upper face of the strips (4) and have lateral flanges (11) in contact to lateral faces of said strips (4), both strips (4) remaining in the same horizontal plane and at a constant separation distance from one another.

A removable closure mechanism (12) comprises two flexible bilateral and parallel strips (13), each provided with a series of snap-fit (14) or magnetic (15) teeth complementary to the teeth of the contralateral strip. The flexible strips (13) rest on the side face of the elastomeric strips (4), and the complementary teeth (14 or 15) are passing through the strips (4) by means of lateral conduits of greatest diameter (7).

A removable adapter element for laparoscopic surgery (16) comprises a lower fixation washer (17) and an upper dome (18). The washer (17) supports its lower face on the stick-to-skin adhesive tape (2), presents a series of magnetic cavities (19) on its upper face, and fits its inner edge on the outer edges of the ends of the elastomeric strips (4). The dome (18) has a convex upper face, a central cylindrical duct running through it vertically, and a flat lower face provided with a series of magnetized reliefs (20) complementary to the magnetized cavities (19) of the upper face of the fixation washer (17).

A removable adapter element for excisional skin surgery comprises an ogive-shaped rigid ring (21) whose external faces are fixed to the inner face of the elastomeric strips (4) by a series of anchoring reliefs (22) which are complementary to the larger diameter ducts (7) of the strips (4). In this way, the incision groove (5) between the elastomeric strips (4) assumes the shape of said ogive-shaped ring (21) which it contains.

Before the placement of the surgical device (1) the partition (8) is placed between the strips (4), occupying the incision groove (5) and the slit (3) of the tape (2). The partition (8) has the function of keeping the strips (4) separated at a precise distance until the device (1) adheres to the skin.

Once the patient is anesthetized and the skin preparation is performed, the release liner is removed from the tape (2) and the device (1) is placed in the selected skin area to make the incision. After the device (1) is firmly attached to the skin, the longitudinal partition (8) is removed and a bare skin surface is inspected at the bottom of the incision groove (5) where the cut will be made. Both the incision and the rest of the intra-operative procedures are carried out according to the conventional technique chosen by the operator, including the hemostatic technique by electrocoagulation and closure of deep planes.

After completing the main surgical procedure and repairing all the subcutaneous planes, the device (1) will be used to close the skin. To close the incision, the teeth (14 or 15) of the removable closure (12) are inserted in the anchorage conduits (7) of each strip (4) until the flexible strips (13) rest on the side walls of the elastomeric strips (4). Finally, the elastomeric strips (4) will be manually compressed together, until the correct anchoring of the complementary teeth (14 or 15) is achieved throughout the entire device (1). The device (1) will remain attached to the skin the same time indicated to maintain a conventional suture. After that period, the tape (2) will be removed in the longitudinal direction and the device (1) will be discarded as a pathogenic residue.

In the event that the device (1) is used as a complement for laparoscopic surgery, the tape (2) adheres to the skin with the fixing washer (17) and the longitudinal partition (8) previously coupled. After the device (1) is firmly attached to the skin, the partition (8) is removed and the incision is made. Once the abdominal cavity is reached, the upper dome (18) of the adapter is attached to the fixation washer (17) and the trocar is inserted to finish forming the laparoscopic access port. Once the laparoscopic surgery is completed, instruments will be removed, then the trocar and finally the adapter (16). The abdominal wall will be sutured by planes with the exception of the skin incision, which will be synthesized by means of the removable closure mechanism (12) of the device (1), as previously described.

In case the device is used as a complement for excisional skin surgery, the device (1) adheres to the skin with the ogive-shaped ring (21) previously attached to the elastomeric strips (4), inside the central incisional groove (5), through its anchoring reliefs (22). Once the tape (2) is adhered to the skin, the incision will be made with the blade of a scalpel following the inner rim of the ogive-shaped ring (21), until the elliptical cut is completed around the lesion that must be removed. Once the perimeter incision is completed, the ogive-shaped ring (21) should be removed to allow dissection of the subcutaneous plane and detachment of the skin patch. Then the subcutaneous tissue will be repaired in a conventional manner, and finally the removable closure mechanism (12) will be coupled to achieve the closure of the skin, as previously described.

What is claimed is:

1. Incision and closure surgical device containing a guide for cutting instruments and a sutureless wound closure mechanism, including a stick-to-skin adhesive tape having a longitudinal central slit which edges are reinforced by two parallel elastomeric strips joined together at their ends, forming an elliptical ring that delimits a central incision groove, which is provided with a mechanical seal for joining said elastomeric strips, comprising:

- a series of lateral conduits that traverse the entire thickness of said elastomeric strips perpendicularly to their major longitudinal axis, communicating said central slit and said central incision groove with lateral faces of said elastomeric strips, being that, some of said lateral conduits are larger-diameter lateral conduits which are distributed interspersed with smaller-diameter lateral conduits throughout the length of said elastomeric strips;
- a removable longitudinal partition or septum, with T-shaped-section segments, which vertical sheets occupy said central slit and said central incision groove, making contact with internal faces of said elastomeric strips, and which horizontal sheets rest on upper faces of said elastomeric strips, and which have two lateral edges that contact said lateral faces of said elastomeric strips, fixing the position of said elastomeric strips in the same horizontal plane and at a distance of constant separation from one another;
- a removable closing mechanism, comprising two flexible strips, bilateral, parallel and complementary to each other, each provided with a series of snap-fit or magnetic teeth, being that said flexible strips rest on said lateral faces of said elastomeric strips, and said snap-fit or magnetic teeth are passing through said elastomeric strips by means of said larger-diameter lateral conduits;
- a removable adapter element for laparoscopic surgery, comprising a lower fixing washer and an upper dome, being that said washer rests its lower face on said stick-to-skin tape, has a series of magnetized cavities on its upper face, and is fixed by its internal edge to the ends of said elastomeric strips, and being that said dome has a convex upper face, a central cylindrical conduit passing through it vertically, and a flat lower face provided with a series of magnetized reliefs complementary to said magnetized cavities of the upper face of said fixing washer;
- a removable adapter element for excisional surgery of skin, comprising a rigid ogive-shaped ring which external faces are fixed on said internal faces of said elastomeric strips by means of a series of reliefs that are complementary to said larger-diameter lateral conduits of said elastomeric strips, so that said central incision groove between said elastomeric strips adopts the shape of said ogive-shaped ring which it contains.

* * * * *